(12) United States Patent
Molis et al.

(10) Patent No.: US 7,932,342 B2
(45) Date of Patent: Apr. 26, 2011

(54) METHOD TO IMPROVE WETTABILITY BY REDUCING LIQUID POLYMER MACROMOLECULE MOBILITY THROUGH FORMING POLYMER BLEND SYSTEM

(75) Inventors: Steven E Molis, Patterson, NY (US); Charles L Reynolds, Red Hook, NY (US); William E Sablinski, Beacon, NY (US); Jiali Wu, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 682 days.

(21) Appl. No.: 12/014,977

(22) Filed: Jan. 16, 2008

(65) Prior Publication Data

US 2009/0182161 A1 Jul. 16, 2009

(51) Int. Cl.
*C08G 77/48* (2006.01)
(52) U.S. Cl. .......................................... 528/31; 528/32
(58) Field of Classification Search .................. None
See application file for complete search history.

(56) References Cited

U.S. PATENT DOCUMENTS

| | | | | |
|---|---|---|---|---|
| 3,491,165 | A * | 1/1970 | Noll et al. | 528/31 |
| 4,714,739 | A * | 12/1987 | Arkles | 525/92 G |
| 4,987,169 | A * | 1/1991 | Kuwata et al. | 524/267 |
| 5,002,818 | A | 3/1991 | Licari et al. | |
| 5,700,581 | A | 12/1997 | Sachdev et al. | |
| 6,172,141 | B1 | 1/2001 | Wong et al. | |
| 6,433,049 | B1 * | 8/2002 | Romenesko et al. | 524/261 |
| 6,498,260 | B2 | 12/2002 | Wang et al. | |
| 6,570,029 | B2 | 5/2003 | Wang et al. | |
| 6,620,308 | B2 | 9/2003 | Gilbert | |
| 6,906,425 | B2 | 6/2005 | Stewart et al. | |
| 6,916,890 | B1 | 7/2005 | Woods et al. | |
| 6,936,664 | B2 | 8/2005 | Woods et al. | |
| 7,230,047 | B2 * | 6/2007 | Issari | 524/500 |
| 7,452,955 | B2 * | 11/2008 | Tanaka et al. | 528/15 |

* cited by examiner

*Primary Examiner* — Marc S Zimmer
(74) *Attorney, Agent, or Firm* — Joseph J. Petrokaitis; Hoffman Warnick LLC

(57) ABSTRACT

A method to reduce liquid polymer macromolecule mobility through forming a polymer blend system is provided. More particularly, a small amount of polymer crosslinker is added to a liquid polymer matrix to prevent intermolecular movement. The crosslinker functions as cages to block linear or branched linear macromolecules and prevent them from sliding into each other.

1 Claim, No Drawings

METHOD TO IMPROVE WETTABILITY BY REDUCING LIQUID POLYMER MACROMOLECULE MOBILITY THROUGH FORMING POLYMER BLEND SYSTEM

BACKGROUND

1. Technical Field

This disclosure relates generally to polymeric fluids, such as silicones, mineral oils, and more particularly, to a process for fabricating a liquid polymer silicone having branched or linear molecular chains with added cross-linked networks.

2. Background Art

Polymer liquids, such as silicone oil and mineral oil, with high thermal stability and low surface tension have been widely used in the manufacture of semiconductors for various applications, including promoting formation of uniform structured film, improving liquid product flow and leveling, and increasing substrate wetting. However, the surface tension of silicone oil and mineral oil is below the average value of common surfaces, which restrict its applications in some particular areas, especially if the area needs stringent chemical migration controls. The disadvantages could include following aspects:

One disadvantage of low surface tension liquids is that it is hard to obtain desired film thickness and to control the wetting area on relevant substrates. Since most polymer liquids are formed by linear macromolecules or branched-linear macromolecules, the polymer chains are prone to sprawling on fresh substrate surfaces once applied. Symmetric chemical structure of silicone leads to low chemical polarity, which contributes to its low surface tension. On fresh substrate surfaces, the fluidic substances with relative lower surface tension have the tendency to cover (coat) its substrate surface for minimizing the internal energy of exposed surface. Over time, the polymer liquid ultimately reaches a thin layer with a relative thickness of a single polymeric macromolecule.

Another disadvantage of low surface tension liquids is that the migration to undesired regions of the surface can cause potential cross-contamination. Migratory liquid thin film could impair bonding adhesion strength to cause hermeticity issue of sealed multichip modules. For reworkable underfill application for MCMs (multichip modules), the uncontrollable wetting on glass ceramic substrates leads to insufficient amount of silicone fluid to underfill the chip C4 gap while thickness becomes critical. As such, alpha particle mitigation capability of reworkable underfill will be impaired during life-long MCM field system application.

On the other hand, fluidic characteristics need to be maintained for certain applications, such as thin gap filling, as well as removal once module repair needs to be done. In view of the foregoing, a need exists to overcome the disadvantages of currently used low surface tension liquids.

SUMMARY

A method to reduce liquid polymer macromolecule mobility through forming a polymer blend system is provided. More particularly, a small amount of polymer crosslinker is added to a liquid polymer matrix to prevent intermolecular movement. The crosslinker functions as cages to block linear or branched linear macromolecules and prevent them from sliding into each other.

A first aspect of the disclosure provides a method for preparing a polymer blend system with crossed-linked networks, the method comprising: mixing crosslinker with a linearly structured polymer to form a mixture; wherein the crosslinker comprising a base agent and a curing agent; wherein the base agent is a silicone with vinyl terminals and the curing agent is a silicone with hydrogen terminals; and curing the mixture.

A second aspect of the disclosure provides a method for preparing a polymer blend system with crossed-linked networks, the method comprising: mixing crosslinker with a linearly structured polymer to form a mixture; wherein the crosslinker comprising a base agent and a curing agent; wherein the base agent is a polyolefin with acid functional groups and the curing agent is a polyolefin with alcohol functional groups; and curing the mixture.

A third aspect of the disclosure provides a polymer blend system with crossed-linked networks which has the following chemical structure:

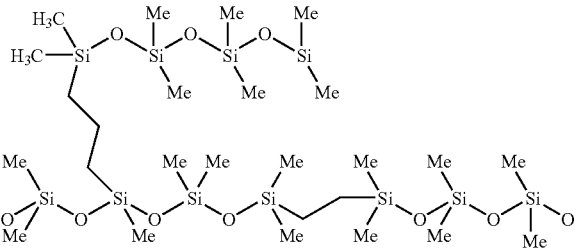

The illustrative aspects of the present disclosure are designed to solve the problems herein described and/or other problems not discussed.

DETAILED DESCRIPTION

An embodiment of the present disclosure provides a method for adding cross-linked networks to a polymer oil to control/reduce the tendency of sprawling of the polymer oil when disposed over surfaces.

Polymer oil, hereinafter referred to as base resin, may include but is not limited to silicone oil, polyolefins, mineral oil or other low surface tension liquids. Polymer oils are usually silicones or mineral oils. Silicones are referred to alternatively as polymerized siloxanes or polysiloxanes, and are represented by the general chemical formula $[R_1R_2SiO]_n$, where $R_1$, $R_2$ represent alkyl groups. Examples of alkyl groups are methyl, ethyl, phenyl and aryl groups. An exemplary example of a base resin is polydimethylsiloxane (PDMS), which has a linear molecular structure:

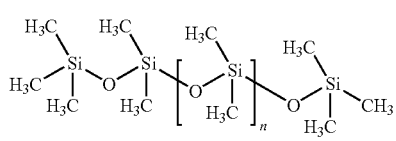

FIG. 1 where n is an integer of SiO(CH$_3$)$_2$ units. Polyolefins, such as mineral oil, may include polyalphaolefins with various polymer molecule weights. Viscosity of polyalphaolefin is commonly used to represent its molecular weight range, which could range from 5 cSt (centi stroke) to 1000 cSt. Other types of polymer fluids could be polyester, or Alkylated Naphthalene, under commercial brand of Esterex and Alkylated Naphthalene from Exxon Mobile.

Cross-linked networks for silicones are formed using crosslinker through additional reactions or reduction reactions. The crosslinker consists generally of two components: a base agent and a curing agent. The base agent may be any silicone with vinyl terminals, or vinyl branches, or both vinyl terminals and branches, herein referred to as vinyl-terminated-silicones, or alkylvinyl or arylvinyl branched siloxane. The base agent may include a vinylmethyl dimethyl copolymer, the copolymer having trimethylsiloxy terminals, or a dimethyl copolymer with vinyl terminals, or a dimethyl dimethylphenyl copolymer with vinyl terminals, or a combination of dimethyl copolymer with vinyl terminals and a dimethyl dimethylphenyl copolymer with vinyl terminals. An exemplary example of a base agent has the following structure:

FIG. 2

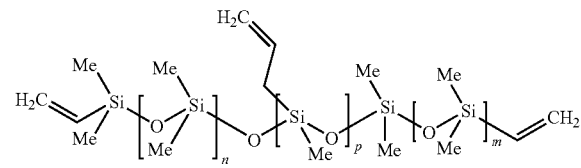

where m=1~10,000, n=1~10,000, p=0~10,000.

The curing agent can be any hydrogen terminated siloxane, or hydrogen branched, or both hydrogen terminated or hydrogen branched, herein referred to as hydrogen-terminated-silicones or methylhydro phenymethyl siloxane or copolymer of the foregoing mentioned. The curing agent may include, for example, but not limited to, phenylhydro phenylmethyl siloxane or methylhydro dimethyl siloxane, having trimethylsiloxyl terminals, or dimethyl siloxane with hydrogen terminals, or a dimethyl dimethylphenyl siloxane with vinyl terminals, or a combination of dimethyl siloxane with hydrogen terminals and a dimethyl dimethylphenyl siloxane with vinyl terminals. An exemplary example of a curing agent is:

FIG. 3

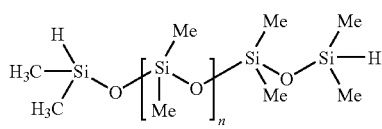

where n=1~1000.

The polymer blend system is formed by adding the base agent to the base resin, followed by the curing agent, to form a mixture. The mixture is then cured at a high temperature. The temperature may range from approximately 80° C. to approximately 165° C. The temperature and time of curing depends on the amount of liquid being cured and curing temperature chosen. For example, the more liquid used, the longer the curing process will take. Likewise, if a higher temperature is used, less time will be needed to cure the liquid.

The resultant polymer blend system is a mixture of linear PDMS doped with cross-linked networks. An example of cured crosslinker is:

FIG. 4: A 3-D Molecular Network Arrangement of Crosslinker After Cure

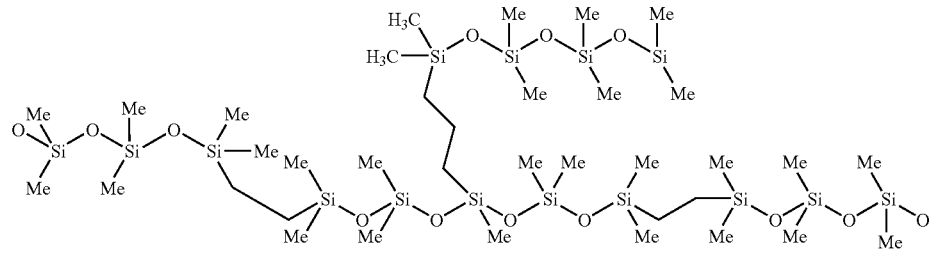

The resulting polymer has a cross-link density that remains low allowing the base resin to retain its liquid state and reworkability (removability) properties. Therefore, the ratio between the base resin (polymer oil) and the crosslinker should preferably be within the range of approximately 30:1 to approximately 1:30. Similarly, the ratio between base agent and curing agent should preferably be within the range of approximately 30:1 to approximately 1:20.

In an alternative embodiment, the crosslinker can consist of different base agents and curing agents. For example, the base agent can consist of an alcohol modified polyolefin, more specifically, an alcohol terminated and/or alcohol side-grouped polyolefin (or polyalcohol). The curing agent can consist of an acid modified polyolefin, more specifically, an acid terminated and/or acid side-grouped polyolefin (or polyacid). In this embodiment, the polyolefin's wetting properties can also be modified by using other crosslinker systems, such as an epoxy/amine system, an epoxy/alcohol system and an epoxy/anhydride system. The polyolefin used in this alternative embodiment may be mineral oil (polyalphaolefin).

As in the embodiments discussed above, the polymer blend system is formed by adding the base agent to the base resin, followed by the curing agent, to form a mixture. The mixture is then cured at a high temperature. The temperature may range from approximately 80° C. to approximately 165° C. The temperature and time of curing depends on the amount of liquid being cured and curing temperature chosen. For example, the more liquid is used, the longer the curing process will take. Likewise, if a higher temperature is used, less time will be needed to cure the liquid. Again, as with the embodiments above, the resultant polymer blend system is a mixture of linear PDMS doped with cross-linked networks.

In this alternative embodiment, using the alcohol and acid modified polyolefins as the base agent and curing agent, respectfully, an esterification reaction occurs while the temperature increases, with water as a byproduct. The water may be removed if desired during the cure process. The reaction generates an ester function group substituted for the ethylene group in the chemical structure illustrated in FIG. 4. For a polyalphaolefin system, a curing agent with polyacrylic acid and polyalcohol is used due to the simplicity of the material blending process control.

The foregoing description of various aspects of the disclosure has been presented for purposes of illustration and description. It is not intended to be exhaustive or to limit the disclosure to the precise form disclosed, and obviously, many modifications and variations are possible. Such modifications and variations that may be apparent to a person skilled in the art are intended to be included within the scope of the disclosure as defined by the accompanying claims.

What is claimed is:

1. A polymer blend system with crossed-linked networks with the following chemical structure:

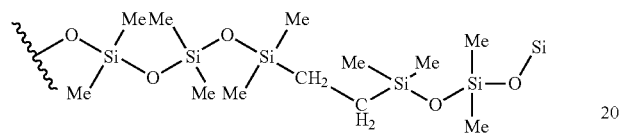

-continued

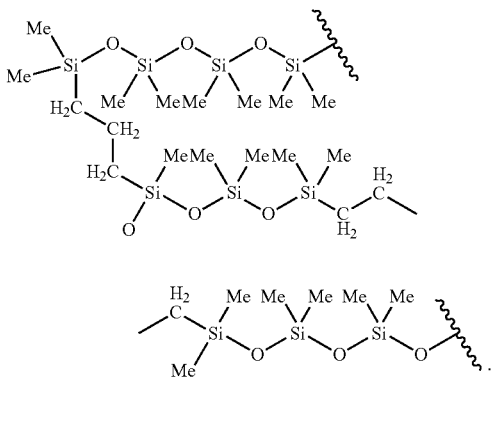

* * * * *